(12) United States Patent
Yoo et al.

(10) Patent No.: US 11,033,531 B2
(45) Date of Patent: Jun. 15, 2021

(54) USE OF CARBAMATE COMPOUND FOR PREVENTING, ALLEVIATING, OR TREATING TREMORS OR TREMOR SYNDROME

(71) Applicant: SK BIOPHARMACEUTICALS CO., LTD., Gyeonggi-do (KR)

(72) Inventors: Jin Uk Yoo, Daejeon (KR); Hye Sung Lee, Daejeon (KR); Han Ju Yi, Gyeonggi-do (KR)

(73) Assignee: SK BIOPHARMACEUTICALS CO., LTD., Gyeonggi- do (KR)

( * ) Notice: Subject to any disclaimer, the term of this patent is extended or adjusted under 35 U.S.C. 154(b) by 0 days.

(21) Appl. No.: 16/468,936

(22) PCT Filed: Dec. 14, 2017

(86) PCT No.: PCT/KR2017/014743
§ 371 (c)(1),
(2) Date: Jun. 12, 2019

(87) PCT Pub. No.: WO2018/111009
PCT Pub. Date: Jun. 21, 2018

(65) Prior Publication Data
US 2019/0336481 A1 Nov. 7, 2019

(30) Foreign Application Priority Data

Dec. 14, 2016 (KR) ........................ 10-2016-0170225

(51) Int. Cl.
*A61K 31/41* (2006.01)
*A61P 25/14* (2006.01)

(52) U.S. Cl.
CPC .............. *A61K 31/41* (2013.01); *A61P 25/14* (2018.01)

(58) Field of Classification Search
CPC ........ A61K 31/41; A61K 31/325; A61P 25/14
See application file for complete search history.

(56) References Cited

U.S. PATENT DOCUMENTS

2002/0151585 A1* 10/2002 Plata-Salaman ........ A61P 25/08
514/483
2006/0258718 A1* 11/2006 Choi ....................... A61P 25/30
514/359

FOREIGN PATENT DOCUMENTS

| CA | 2776743 C | * | 3/2017 | ........... C07D 257/04 |
|----|-----------|---|--------|------------------------|
| KR | 10-2010-0137389 A | | 12/2010 | |
| KR | 10-2012-0087124 A | | 8/2012 | |
| KR | 10-1286499 B1 | | 7/2013 | |
| KR | 10-2017-0131242 A | | 11/2017 | |
| WO | WO-02/067926 A1 | | 9/2002 | |
| WO | WO-2005-097136 A1 | | 10/2005 | |
| WO | WO-2006/112685 A1 | | 10/2006 | |

(Continued)

OTHER PUBLICATIONS

Elan D Louis, Essential tremor, Lancet Neurol., 2005, 4, 100-110.
(Continued)

*Primary Examiner* — San Ming R Hui
(74) *Attorney, Agent, or Firm* — Harness, Dickey & Pierce, P.L.C.

(57) ABSTRACT

The present invention relates to a use of a pharmaceutical composition which includes a carbamate compound of chemical formula 1 and is administered to prevent, alleviate, or treat tremors or tremor syndrome.

10 Claims, 1 Drawing Sheet

* $p<0.05$, ** $p<0.01$ vs Vehicle/Oxotremorine

(56) References Cited

FOREIGN PATENT DOCUMENTS

| WO | WO-2010/150946 A1 | 12/2010 |
| WO | WO-2011/046380 A2 | 4/2011 |
| WO | WO-2014/142518 A1 | 9/2014 |
| WO | WO-2017/200318 A1 | 11/2017 |

OTHER PUBLICATIONS

JN Panicker, PK Pal, Clinical Features, Assessment and Treatment of Essential Tremor, JAPI, 2003, 51, 276-279.
Hao Deng, Weidong Le, Joseph Jankovic, Genetics of essential tremor, Brain, 2007, 13, 1456-1464.
Elan D Louis, Jean Paul G Vonsattel, The Emerging Neuropathology of Essential Tremor, Mov. Disord., 2008, 23, 174-182.
T.J. Murray, Essential tremor, 1981, CMA Journal, 1981, 124, 1559-1570.
Mark Lees, Loren Regier, Brent Jensen, Pharmacologic management of essential tremor, Canadian Family Physician, 2010, 56, 250-252.
B Cox, D Potkonjak, Effects of drugs on tremor and increase in brain acetylcholine produced by oxotremorine in the rat, Br. J. Pharmac., 1970, 38, 171-180.
International Search Report from corresponding PCT Application No. PCT/KR2017/014743, dated Mar. 19, 2018.
Extended European Search Report from corresponding European Patent Application No. 17880232.8, dated May 18, 2020.

\* cited by examiner

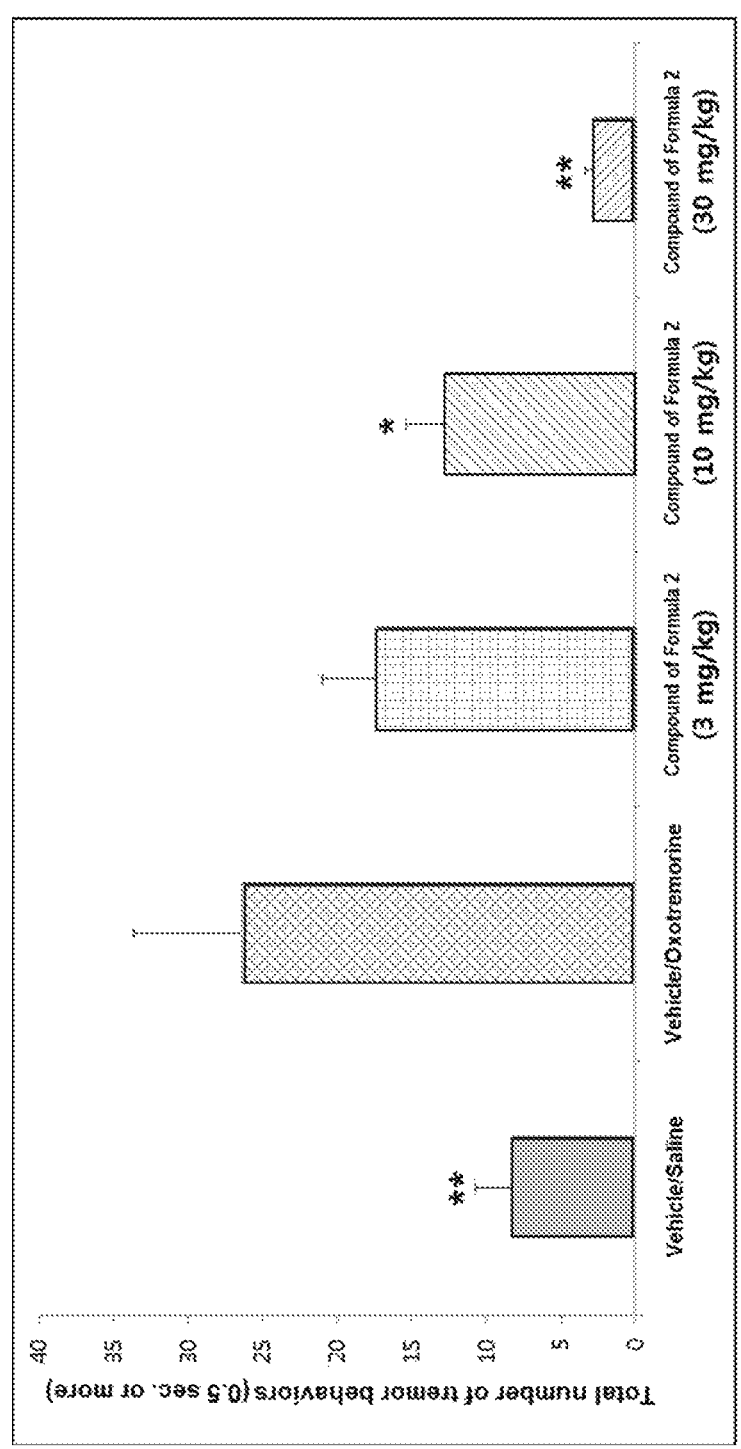

USE OF CARBAMATE COMPOUND FOR PREVENTING, ALLEVIATING, OR TREATING TREMORS OR TREMOR SYNDROME

CROSS-REFERENCE TO RELATED APPLICATIONS

This application is a national phase application of PCT Application No. PCT/KR2017/014743, filed on 14 Dec. 2017, which claims the benefit and priority to Korean Patent Application No. 10-2016-0170225, filed on 14 Dec. 2016. The entire disclosures of the applications identified in this paragraph are incorporated herein by references.

FIELD

The present invention relates to use of a carbamate compound of the following Formula 1 for the purpose of preventing, alleviating or treating tremor or tremor syndrome by administering a pharmaceutical composition comprising said carbamate compound:

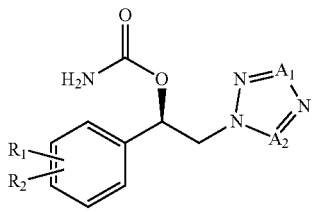

[Formula 1]

wherein,
$R_1$, $R_2$, $A_1$ and $A_2$ are as defined herein.

BACKGROUND

Tremor or oscillation is a symptom in which a body part shakes regularly even though it was not intended. Medically, tremor is defined as an involuntary and rhythmic oscillatory movement of a part or parts of the body, resulting from alternating or irregularly synchronous contractions of antagonist muscles. Tremor can occur due to normal physiological processes, pathologic mechanisms or the uptake of certain medications and can be exacerbated by stress, anxiety, fatigue, coffee or tobacco.

Tremors are largely divided into two types; rest tremors and action tremors. Rest tremor occurs when muscle is not voluntarily activated, whereas action tremor is present with voluntary contraction of muscle. Subtypes of action tremor include postural, kinetic and isometric tremor. Postural tremor is present while voluntarily maintaining a position against gravity. Kinetic tremor may occur during any form of voluntary movement. Isometric tremor occurs when an equal degree of muscle contraction occurs for an object, such as holding the tester's hand tightly. Kinetic tremor includes (a) simple kinetic tremor that is present with non-target-directed autonomous action, (b) intention tremor referring to exacerbation of kinetic tremor toward the end of a goal-directed movement and (c) task-specific kinetic tremor that occurs during performance of certain tasks and activities.

Since practical classifications of tremor that are based upon etiologic or pathophysiologic factors are not currently available, tremor or tremor syndrome is generally classified on the basis of the clinical symptoms (syndrome) of tremor.

1) Essential tremor: Oscillation appears only when stretching the arms or hand writing, while it does not appear at all when the muscles or limbs are resting. Enhanced physiologic tremor can be easily removed when the cause is removed, whereas in the case of essential tremor, it appears consistently regardless of changes in the situation. Essential tremor includes familial tremor, essential tremor, senile tremor and the like.

2) Physiologic tremor: A normal phenomenon, physiologic tremor occurs in all contracting muscle groups. During contraction of the exercise unit to contract a muscle, there is a slight temporal difference and a slight and imperceptible muscle shake. Although seldom visible to the naked eye, physiologic tremor has a frequency in the range of 8 Hz to 13 Hz, and thus is subtly detectable on electromyography (EMG).

3) Enhanced physiologic tremor: The amplitude of the physiologic tremor is intensified for some reason so as to be seen by the naked eye. Enhanced physiologic tremor refers to such an oscillation that appears as a symptom. This may occur in all people, and the physiologic tremor may be enhanced under conditions of anxiety and nervousness, stage fright, stress, fatigue, exercise, cold, hunger, stimulant use and alcohol withdrawal, or metabolic disorders such as hypoglycemia or hyperthyroidism.

4) Parkinsonian tremor syndrome: It is the most characteristic tremor observed in patients with Parkinson's disease, a slow tremor at the fingertip when the patient is sitting or walking. This tremor is mainly seen when the patient is resting and is diminished or disappears during any intended action. This is a typical (representative) resting tremor and is a degenerative disorder of the central nervous system (CNS) that may be characterized by rigidity, and bradykinesia or slowness and poverty of movement.

5) Psychogenic tremor: It is also referred to as a hysterical tremor wherein tremor occurs rarely for the purpose of a secondary benefit or without any reason. One of the observations of patients with this tremor is that tremor disappears when the patient thinks that there is no one around him/her or when the patient's attention is shifted away from the area where the tremor is present.

6) Cerebellar tremor syndrome: It is also referred to as intention tremor wherein irregular tremor appears temporarily when a behavior continues or fine adjustment is needed, which make the intended behavior difficult, resulting in disability in some experienced behavior that the patient has been through previously. This type of tremor is almost always caused by abnormalities in the cerebellum or the connecting part with the cerebellum.

7) Drug-induced and toxic tremor syndromes: Pharmacologic agents used to treat other medical conditions may induce tremor. Such medications may include theophylline, valproate, lithium, tricyclic antidepressants, neuroleptics, sympathomimetics, amphetamines, steroids, and certain agents used to treat endocrine and metabolic disorders. Toxic tremor, such as seen in manganese, arsenic, or mercury intoxication or poisoning, occurs in association with other neurologic symptoms, such as gait disturbances, rigidity, dystonia, ataxia, dysarthria, confusion, etc. Alcohol withdrawal tremor due to alcohol withdrawal may also be included.

8) Primary orthostatic tremor: This is a postural tremor of lower limb, trunk and upper limb muscles while standing, yet it is absent when sitting or reclining. In most patients, orthostatic tremor is suppressed upon walking. As seen on EMG, orthostatic tremor is characterized by high frequency, 13 Hz to 18 Hz entrainment of synchronous motor unit activity of contralateral and ipsilateral muscles, primarily of the lower limbs.

9) Undetermined tremor syndrome: Patients with indeterminate tremor syndrome fulfill the criteria for classic essential tremor (ET) yet have additional neurologic signs.

10) Dystonic tremor: This refers to primarily postural and kinetic tremor occurring in a body part affected by dystonia.

11) Task- and position-specific tremors: These tremors occur upon performance of specific, highly specialized motor activities. They include primary writing tremor, defined as tremor occurring solely or primarily while writing yet not with other hand activities; occupational tremors, such as specific tremors affecting athletes or musicians; or isolated voice tremors.

12) Holmes tremor: This is traditionally known as rubral or midbrain tremor. Holmes tremor is defined as a symptomatic rest tremor, intention tremor and postural tremor due to lesions affecting the cerebellothalamic system and the dopaminergic systems, such as involving the brainstem, cerebellum and thalamus.

13) Palatal tremors: This refers to rhythmic movements of the soft palate occurring subsequent to lesions of the brainstem and cerebellum. It may or may not be associated with olivary pseudohypertrophy.

14) Neuropathic tremor syndrome: This refers to a kinetic and postural tremor in limb area that is primarily affected by certain peripheral neuropathies, particularly dysgammaglobulinemic neuropathies.

15) Myorhythmia: A slow tremor of 2 Hz to 4 Hz as seen in patients with lesions of the brainstem which is similar to Holmes tremor.

Essential tremor is a neurologic movement disorder with oscillating movements of unknown cause, often causing functional disorders and potentially physiological and emotional disorders. Essential tremor usually occurs in the hands, but can uncommonly occur in the head, legs or voice, which affects daily life (Elan D Louis, Essential tremor, Lancet Neurol., 2005, 4, 100-110). The characteristic of essential tremor is the regular oscillating movements that occur during the exercise of a voluntary muscle or while maintaining the force against gravity. Essential tremor is often misdiagnosed as Parkinson's disease because in the case of Parkinson's disease the body is stiffened and slowed, and hand shaking symptoms may appear.

Essential tremor is the most common type tremor among more than 20 types. Essential tremor occurs 10 to 20 times more frequently than Parkinson's disease (PD), affecting 5 million to 10 million people in the United States alone. Although the average age of onset of essential tremor is usually 40, it may occur first in other age groups such as children and the elderly (J N Panicker, P K Pal, Clinical Features, Assessment and Treatment of Essential Tremor, JAPI, 2003, 51, 276-279).

Although the cause of essential tremor is not well known, genetic relevance has often been reported as the cause in view of most patients' findings. However, even in the absence of family history, essential tremor may be developed. The epidemiological relevance of essential tremor is known to be due to the occurrence of abnormal signal transduction between specific parts of the brain, including the cerebellum, thalamus and brainstem (Hao Deng, Weidong Le, Joseph Jankovic, Genetics of essential tremor, Brain, 2007, 13, 1456-1464; Elan D Louis, Jean Paul G Vonsattel, The Emerging Neuropathology of Essential Tremor, Mov. Disord., 2008, 23, 174-182).

As tremors are of various types, there are differences in their treatment methods, and the response to such treatments varies. There is no FDA-approved drug for the treatment of essential tremor, and drugs approved for the treatment of other diseases are used for tremor therapy, and its use is limited due to its efficacy and side effects. Beta-adrenoreceptor antagonists such as propranolol are known to weaken essential tremor and physiologic tremor, but may also affect the central nervous system (T. J. Murray, Essential tremor, 1981, CMA JOURNAL, 1981, 124, 1559-1570).

Most essential tremor patients benefit from pharmacological therapy, and many experience a significant reduction of tremor. However, it is very rare that tremor is completely diminished, and none of the drugs work effectively for all patients. In addition, tolerance may be reported in some patients undergoing long-term therapy, by which the patients may experience rather worsening of the symptoms of tremor.

In addition, there are still limitations in the use of the drugs due to the comorbidities associated with them which result in an unsatisfactory level of therapeutic effect or due to side effects. Thus, there is a need for new drugs with improved efficacy and fewer side effects (Mark Lees, Loren Regier, Brent Jensen, Pharmacologic management of essential tremor, Canadian Family Physician, 2010, 56, 250-252).

SUMMARY

Problem to be Solved

The present invention is intended to provide a method for the prevention, alleviation or treatment of tremor or tremor syndrome, particularly essential tremor.

The present invention is also intended to provide the use of a carbamate compound of the following Formula 1, or a pharmaceutically acceptable salt, solvate or hydrate thereof, for the prevention, alleviation or treatment of tremor or tremor syndrome, particularly essential tremor:

[Formula 1]

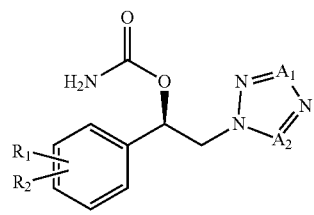

wherein, $R_1$, $R_2$, $A_1$ and $A_2$ are as defined herein.

Technical Solution to the Problem

The present invention provides a medicament for the prevention, alleviation or treatment of tremor or tremor syndrome, particularly essential tremor, comprising a therapeutically effective amount of a carbamate compound of the following Formula 1, or a pharmaceutically acceptable salt, solvate or hydrate thereof:

[Formula 1]

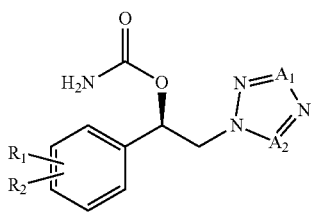

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In addition, the present invention provides a pharmaceutical composition for the prevention, alleviation or treatment of tremor or tremor syndrome, particularly essential tremor, comprising a therapeutically effective amount of the carbamate compounds of the above Formula 1, or a pharmaceutically acceptable salt, solvate or hydrate thereof, and further one or more of a pharmaceutically acceptable carrier.

In addition, the present invention provides a method for preventing, alleviating or treating tremor or tremor syndrome, particularly essential tremor, in a subject, comprising administering to the subject a therapeutically effective amount of the carbamate compounds of the above Formula 1, or a pharmaceutically acceptable salt, solvate or hydrate thereof.

In addition, the present invention provides the use of the carbamate compounds of the above Formula 1, or a pharmaceutically acceptable salt, solvate or hydrate thereof for the prevention, alleviation or treatment of tremor or tremor syndrome, particularly essential tremor, or for the improvement of symptoms associated with them.

In one embodiment of the present invention, in the above Formula 1, $R_1$ and $R_2$ are each independently selected from the group consisting of hydrogen, halogen and $C_1$-$C_8$ alkyl.

In one embodiment of the present invention, the halo $C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl)ethyl ester of the following Formula 2:

[Formula 2]

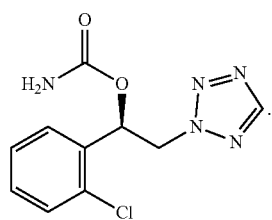

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in PCT Publication Nos. WO 2006/112685 A1, WO 2010/150946 A1 and WO 2011/046380 A2, the disclosures of which are incorporated herein by reference. The compounds of the above Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

The carbamate compounds of the above Formula 1 can be used for the prevention, alleviation or treatment of tremor or tremor syndrome.

Particularly, the carbamate compounds of the above Formula 1 can be used for the prevention, alleviation or treatment of essential tremor.

According to one embodiment of the present invention, tremor or tremor syndrome includes rest tremor, action tremor and combined (complex) tremor thereof.

Rest tremor includes Parkinsonian tremor syndrome, myorhythmia, cerebellar tremor syndrome, neuropathic tremor syndrome, psychogenic tremor and the like.

Action tremor may be classified as postural tremor, kinetic tremor and isometric tremor. Postural tremor includes essential tremor, physiologic tremor, enhanced physiologic tremor, dystonic tremor and the like. Kinetic tremor includes simple kinetic tremor, intention tremor, task-specific kinetic tremor and the like, and also includes cerebellar tremor syndrome, palatal tremor, partially neuropathic tremor syndrome, drug-induced and toxic tremor syndrome, myorhythmia, psychogenic tremor and the like. Isometric tremor includes primary orthostatic tremor and the like. Other complex tremors that do not belong to the aforementioned tremors include Holmes tremor, palatal myoclonus and the like.

As an example of a model for assessing the potential efficacy of therapeutic agents that can effectively treat tremor and other tremor syndromes, including essential tremor, oxotremorine-induced tremor in animals can be used (B Cox, D Potkonjak, Effects of drugs on tremor and increase in brain acetylcholine produced by oxotremorine in the rat, Br. J. Pharmac., 1970, 38, 171-180).

The dosage of the carbamate compounds of Formula 1 for the prevention, alleviation or treatment of the above diseases may typically vary depending on the severity of the disease, the body weight and the metabolic status of the subject. A "therapeutically effective amount" for an individual patient refers to an amount of the active compound sufficient to achieve the above pharmacological effect, i.e., the therapeutic effect as described above. The therapeutically effective amount of the compounds of the present invention is 50 to 500 mg, 50 to 400 mg, 50 to 300 mg, 100 to 400 mg, 100 to 300 mg, 50 to 200 mg, or 100 to 200 mg, based on the free form and once-daily administration to humans. The therapeutically effective amount is preferably 50 to 300 mg, more preferably 50 to 200 mg.

The compounds of the present invention may be administered by any conventional method used for administration of a therapeutic agent, such as oral, parenteral, intravenous, intramuscular, subcutaneous or rectal administration.

The medicament or pharmaceutical composition according to one embodiment of the present invention may comprise a therapeutically effective amount of a compound selected from the group consisting of the carbamate compounds of the present invention, their pharmaceutically acceptable salts, solvates, hydrates and combinations thereof.

Examples of the pharmaceutically acceptable salts of the carbamate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemisuccinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc.

The medicament or pharmaceutical composition according to one embodiment of the present invention may be administered orally or parenterally. The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In the case of oral administration, the pharmaceutical composition according to one embodiment of the present invention may be formulated as a plain tablet (uncoated tablet) or such that the active agent is coated or it is protected against degradation in the stomach. In addition, the composition can be administered by any device capable of transferring the active substance to a target cell. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skill can easily determine and prescribe dosages that are effective for the desired treatment or prophylaxis. The pharmaceutical composition according to one embodiment may be administered in one or more doses, for example, one to four times per day. The pharmaceutical composition according to one embodiment may contain the compounds of Formula 1 in the amount of 50 to 500 mg, 50 to 400 mg, 50 to 300 mg, 100 to 400 mg, 100 to 300 mg, 50 to 200 mg, or 100 to 200 mg, preferably 50 to 300 mg, more preferably 50 to 200 mg, based on the free form.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents, and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivatives (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

As used herein, the terms "prevent," "preventing" and "prevention" refer to reducing or eliminating the likelihood of a disease.

As used herein, the terms "alleviate," "alleviating" and "alleviation" refer to ameliorating a disease and/or its accompanying symptoms altogether or in part.

As used herein, the terms "treat," "treating" and "treatment" refer to eliminating a disease and/or its accompanying symptoms altogether or in part.

As used herein, the term "subject" refers to an animal that is the object of therapy, observation or experiment, preferably a mammal (such as primates (e.g., a human), cattle, sheep, goats, horses, dogs, cats, rabbits, rats, mice, etc.), most preferably a human.

As used herein, the term "therapeutically effective amount" refers to the amount of active compound or pharmaceutical formulation that elicits a biological or medical response in the system, animal or human, including alleviation of the symptoms of the disease or disorder to be treated, wherein said amount is sought by a researcher, veterinarian, doctor (physician) or other clinician.

As used herein, the term "composition" encompasses a product that contains a specified amount of a particular ingredient and any product that results directly or indirectly from a combination of specified amounts of particular ingredients.

Effect of the Invention

The medicament and the pharmaceutical composition according to the present invention can effectively treat and prevent tremor or tremor syndrome, especially multiple essential tremor.

BRIEF DESCRIPTION OF THE DRAWINGS

FIG. 1 is a graph showing the results of the oxotremorine-induced tremor experiments performed in Example 1.

DETAILED DESCRIPTION

Hereinafter, the present invention will be explained in more detail through working examples. However, the following working examples are only intended to illustrate one or more embodiments and are not intended to limit the scope of the invention.

Preparation Example: Synthesis of Carbamic Acid (R)-1-(2-chlorophenyl)-2-tetrazol-2-yl)ethyl ester Carbamic acid (R)-1-(2-chlorophenyl)-2-tetrazol-2-yl) ethyl ester (the compound of Formula 2, hereinafter referred to as "the test compound") was prepared according to the method described in Preparation Example 50 of PCT Publication No. WO 2010/150946.

Example 1: Effect on Oxotremorine-Induced Tremor in Rats

Oxotremorine-Induced Tremor

As a model for assessing the potential efficacy of therapeutic agents that can effectively treat essential tremor and other tremor syndromes, oxotremorine-induced tremor in rats was used [B Cox, D Potkonjak, Effects of drugs on tremor and increase in brain acetylcholine produced by oxotremorine in the rat, Br. J. Pharmac., 1970, 38, 171-180].

Male SD rats (CrjBgi:CD(SD)IGS) were purchased from Orient Bio, Inc. of Korea, and placed in a wire mesh cage under conditions of ambient temperature of 20 to 24° C., 55 to 75% relative humidity, an automatically controlled light-and-darkness cycle of 12 hours and free access to feed (purchased from Agri Brands Purina Korea, Inc.) and water. The rats were housed and maintained in accordance with the Laboratory Animal Care Standards of the Institutional Animal Care and Use Committee (IACUC). After about one week of stabilization, rats weighing 200 to 240 g were used in the experiment. The rats to be used for the experiment were fasted by removing the feed 16 hours before the experiment, and placed in a tremor measurement device (Tremor Monitor™, San Diego Instruments, CA) 3 hours before the experiment and adapted for 10 minutes.

The test compound was prepared by dissolving it in 30% polyethylene glycol 400 (purchased from Sigma) used as a vehicle 30-45 minutes before each experiment. The vehicle and the test compound (3, 10 and 30 mg/kg dose) were administered into the oral cavity, respectively, in a volume of 4 ml per 1 kg body weight of the rat. After 60 minutes, oxotremorine (oxotremorine sesquifumarate salt, 1-(4-[1-Pyrrolidinyl]-2-butynyl)-2-pyrrolidinone sesquifumarate; purchased from Sigma) dissolved in saline and prepared in a volume of 1 mg/kg or a saline were subcutaneously injected into the back of the rat neck in a volume of 2 ml per 1 kg body weight of the rat. Oxotremorine-administered rats were immediately placed in a tremor measurement device (filter frequency 12 Hz, band-width 6 Hz, filter number 2), and the number of tremor behaviors that progressed for at least 0.5 seconds in 2,048 seconds were automatically measured and recorded. The number of rats per group was 16.

Statistical Analysis of the Experiment Results

All data were expressed as mean±SEM. The number of oxotremorine-induced tremor behaviors in the group treated with the test compound was expressed as % inhibition compared to the vehicle group. Statistical analysis of the number of tremor behaviors between groups was performed using one-way ANOVA (one-way analysis of variance) and Dunnett's multiple comparison test by using the GraphPad Prism ver. 4.0 program. The mean number of tremor behaviors in the vehicle/oxotremorine group was observed as 29.8±8.1, and the mean number of tremor behaviors in the vehicle/saline group was observed as 9.2±2.5. In the test compound administered group, tremor behaviors were inhibited in a dose dependent manner, showing inhibition rates of 50.3% at 3 mg/kg, 78.7% at 10 mg/kg and 130.4% at 30 mg/kg. Median Effective Dose ($ED_{50}$) value was calculated to be 1.67 mg/kg. The test compound showed significant pharmacological activity in the oxotremorine-induced tremor behavior model, which is a representative animal model of essential tremor syndrome. Table 1 summarizes the experimental data (inhibition rate), and the experimental results are shown in FIG. 1.

TABLE 1

| Agents treated | Dose (mg/kg, p.o.) | Number of animals | Number of tremor behaviors | Inhibition rate compared to negative group[3] | Calculated Median Effective Dose ($ED_{50}$) |
|---|---|---|---|---|---|
| Vehicle/Saline | 0 | 16 | 9.2 ± 2.5[1] | — | — |
| Vehicle/Oxotremorine | 0 | 16 | 29.8 ± 8.1 | 0.0% | — |
| Test compound/Oxotremorine | 3 | 16 | 19.4 ± 3.7 | 50.3% | 1.67 mg/kg, p.o. |
|  | 10 | 16 | 13.6 ± 0.1[2] | 78.7% |  |
|  | 30 | 16 | 2.9 ± 0.5[1] | 130.4% |  |

[1]Significance of the number of tremor behaviors compared to the negative control group: p < 0.01
[2]Significance of the number of tremor behaviors compared to the negative control group: p < 0.05
[3]Calculation of inhibition rate compared to the negative control group = − [(Mean number of tremor behaviors of compound of Formula 2/oxotremorine group − Mean number of tremor behaviors of vehicle/saline group)/(Mean number of tremor behaviors of vehicle/oxotremorine group − mean number of tremor behaviors of vehicle/saline group) − 1] × 100

What is claimed is:

1. A method for alleviating or treating tremor or tremor syndrome in a subject, comprising administering to the subject a therapeutically effective amount of a carbamate compound of the following Formula 1, or a pharmaceutically acceptable salt, solvate or hydrate thereof:

[Formula 1]

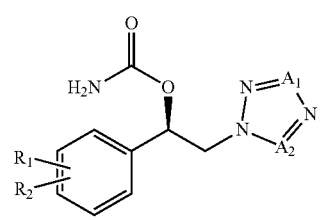

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

2. The method according to claim 1, wherein $R_1$ and $R_2$ are each independently selected from the group consisting of hydrogen, halogen and $C_1$-$C_8$ alkyl.

3. The method according to claim 1, wherein the carbamate compound of Formula 1 is carbamic acid (R)-1-(2-chlorophenyl)-2-tetrazol-2-yl)ethyl ester of the following Formula 2:

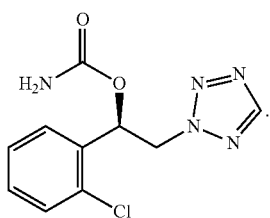

[Formula 2]

4. The method according to claim 1, wherein the method is for the alleviation or treatment of essential tremor.

5. The method according to claim 1, wherein the tremor or tremor syndrome is rest tremor, action tremor or combined (complex) tremor thereof.

6. The method according to claim 5, wherein the rest tremor is one or more selected from the group consisting of Parkinsonian tremor syndrome, myorhythmia, cerebellar tremor syndrome, neuropathic tremor syndrome and psychogenic tremor; and the action tremor is one or more selected from the group consisting of postural tremor, kinetic tremor and isometric tremor.

7. The method according to claim 1, wherein the tremor or tremor syndrome is one or more selected from the group consisting of Parkinsonian tremor syndrome, myorhythmia, cerebellar tremor syndrome, neuropathic tremor syndrome, psychogenic tremor, essential tremor, physiologic tremor, enhanced physiologic tremor, dystonic tremor, simple kinetic tremor, intention tremor, task-specific kinetic tremor, palatal tremor, drug-induced and toxic tremor syndrome, primary orthostatic tremor, Holmes tremor and palatal myoclonus.

8. The method according to claim 1, wherein the subject is a mammal.

9. The method according to claim 8, wherein the mammal is a human.

10. The method according to claim 1, wherein the therapeutically effective amount of the carbamate compound of Formula 1 is 50 mg to 500 mg based on the free form.

* * * * *